United States Patent [19]

Hickham

[11] Patent Number: 4,501,554
[45] Date of Patent: Feb. 26, 1985

[54] TWO TRAY INDIRECT BONDING SYSTEM FOR LABIAL AND LINGUAL BRACKETS

[76] Inventor: John H. Hickham, 325 23rd St., Kenner, La. 70062

[21] Appl. No.: 516,906

[22] Filed: Jul. 25, 1983

[51] Int. Cl.³ .............................................. A61C 3/00
[52] U.S. Cl. ......................................... 433/24; 433/3; 433/9
[58] Field of Search ................................ 433/3, 9, 24

[56] References Cited

U.S. PATENT DOCUMENTS

| | | | |
|---|---|---|---|
| 3,738,005 | 6/1973 | Cohen et al. | 433/24 |
| 4,284,405 | 8/1981 | Dellinger | 433/3 |
| 4,360,341 | 11/1982 | Dellinger | 433/24 |

*Primary Examiner*—Gene Mancene
*Assistant Examiner*—David I. Tarnoff
*Attorney, Agent, or Firm*—C. Emmett Pugh & Associates

[57] ABSTRACT

A method for transferring brackets for the teeth from a prepared carrier tray system to the teeth of the patient using an improved two tray system. The brackets are fitted over the teeth of the patient with the intention of using these brackets as a base for attaching other orthodontic equipment. The first tray is of a flexible nature which can be made to retain its original shape after placing brackets on the teeth in a predetermined ideal position. The second tray is a more rigid tray which is inserted over the first tray. The second tray stabilizes the seating of the brackets during seating or drying of the cement securing the brackets.

5 Claims, 1 Drawing Figure

TWO TRAY INDIRECT BONDING SYSTEM FOR LABIAL AND LINGUAL BRACKETS

BACKGROUND OF INVENTION

1. Field of Invention

The present invention relates to techniques for positioning and securing orthodontic brackets. More particularly, the present invention relates to a method for placing and securing orthodontic brackets utilizing an outside replica model of the patient's teeth for pre-positioning the brackets, followed by the transfer from the model to the patient's teeth, utilizing a two tray system for transferring the brackets, one of the trays being a soft tray and the other being a more rigid tray.

2. Prior Art

Positioning of dental or orthodontic mounting brackets of various types, known commonly as braces, on the teeth of a patient for correcting various irregularities is well known in the dental art. These brackets may be of several types. In most older work, entire bands were placed around the teeth, each band being equipped with a protuberance to which wires or bands could be attached in order to link the system of brackets and to allow proper correction of the patient's teeth. Other techniques include the use of brackets which are plates with attached protruberances which function as the previous bands but which are attached by cementing these brackets were needed to the face of the teeth, eliminating the need for bands encircling the teeth with the associated complications.

Also well known in the art is the use of models or dental casts made identical to the patient's teeth for determining the placing of the brackets. These casts are also used for other purposes known in the art.

The technique for placing brackets on teeth has been accomplished by individually placing brackets on the model and then removing them one at a time to be placed on the patient. It is also known in the art to use a single molded positioning cast to move the brackets as a unit from the dental cast to the patient's teeth.

In the latter technique, the brackets are first put on the dental cast. Next, a single positioner or "tray" is molded around the brackets and dental cast, so that, when the positioner is allowed to set and is removed, it also removes the brackets. This mold can then be put over the patient's teeth where they are cemented on. See U.S. Pat. No. 3,738,005 issued June 12, 1973 to Cohen et al.

The problem with the original tray system lies partially in the lack of flexibility in the system. The original tray had to be rigid enough to hold on to the teeth aiding in bracket placement. It also had to be flexible enough to fit over malposed teeth. This inconsistency was further exacerbated by the fact that the flexibility destroyed the assurance of accurate placement, since the original tray would become at least slightly distorted during placement of the tray over the teeth or even earlier when it is removed from the dental cast.

The problems caused due to the inherent flight between the two inconsistent goals of flexibility and rigidity were magnified by the fact that the process requires time for setting, and any deviation from the desired placement could cause potential doubling or worse of the time required to properly place the brackets. Or worse still, it could lead to the use of the improperly placed brackets in order to correct the patient's orthodontic problem with less than perfect results.

It is the goal of the present method to improve on the method for transferring brackets using a prepared carrier tray system from a dental cast or other arranging means to the patient's teeth.

It is also the goal of the present invention of make the profile of the cast lower, decreasing the bulk and hence increasing the ease with which the device is used by the treating physician and decreasing the discomfort of the patient and decreasing generally the time required for the entire operation.

It is also the goal of the present invention to allow a wider range of possible molding agents to be used than was consistent with the older methods in the art by decreasing the requirements put on the material used. This further allows the use of clear molding agents, allowing the treating physician to more closely follow the procedure.

It is also a goal to allow the use of more flexible primary trays, which actually contact the teeth to allow greater adjustment when the trays are actually in place.

It is also the goal of the present invention to provide a two tray, indirect bonding system for labial and lingual brackets, which is more easily used and less likely to cause mistakes and wasted time than the previously known single tray systems.

3. General Discussion of the Invention

As with the prior art, it is important that the patient be properly prepared before the brackets are implaced. In this invention, the preparation includes thoroughly cleaning the patients teeth, especially to ensure that there are no concretions or calculus build up on the teeth. It is important that no radical actions are taken which would result in a large change or movement of the teeth, such as by extraction of other teeth or separations of the teeth, between the time of making impressions and the time or seating of the indirect bonding trays. It is, however, one of the benefits of this system that it is more fit for for use where the normal and minor changes require some flexibility in the fitting of the trays over the malpositioned teeth.

Alginate impression are taken using procedures well known in the art. It is important that these impressions accurately reproduce the palate and all the tooth surfaces with clear definition of the gingival crest. Models are poured in these impressions, usually in yellow stone. Only these original models are acceptable due to the accuracy desired. Additionally, these models should be free of bubbles, chips, voids or other deformaties and should be trimmed if possible. The models are usually placed in a flat base so that accurate measurements may be made prior to the placement of the brackets on the model for later removal to the teeth.

At this point, the actual seating of the dental trays may be performed. The two tray procedure incorporates the advantage of allowing for the brackets and trays to be mounted on the dental cast either at the dental office or in another location.

The bonding system consists of two trays, one hard and the other soft as described in more detail below. The hard tray serves to hold the soft tray in its shape, after the soft tray is removed from the dental cast. The soft tray can be made in the same manner as the original mold for the dental cast, by pouring the soft tray material into containers which in turn is placed over the teeth or in this case the dental cast. The hard tray is made in such a manner as to hold the shape of the soft cast after it is in place.

Seating the trays is accomplished by preparing the patient in the manner used for direct bonding. First the teeth are pumiced, dried, etched, dried and sealed. It should be understood, of course, that other methods known in the art might be used.

Next a syringe is used to apply bonding material to the bracket base or the place on the teeth where the bracket base is to be set. The primary tray, described in detail below, is then placed in the patient's mouth. Due to the lack of rigidity necessary, the tray may be thin for easy and quick placing. It is usually suggested that the tray be placed buccally first, as it is the labial tray, preventing wiping of bonding material from the bases of the brackets. The secondary tray can then be immediately placed to insure proper seating without improper movement of the soft tray relative to the teeth.

The hard tray removes easily after the seating has occurred by the drying of the seating compound. The soft tray can then be removed, this being eased by the softness of the material involved.

The present invention provides a unique and improved method of transferring brackets from a prepared carrier tray system to the patient's teeth.

The advantage of the two tray system of the present invention over the previous one tray, indirect bonding system is that the previous original tray system had to be rigid enough to hold on to the teeth aiding in bracket placement. Since this tray had to be slightly flexible (to fit over malposed teeth) yet rigid enough to stay on the teeth, bracket placement to the patients teeth was not always accurate since the original tray would become slightly distorted during placement of the tray to the teeth.

The two tray system of the present invention virtually eliminates distortion during insertion of the trays into the mouth and over the teeth, which caused the brackets to be misplaced or drift from their ideal position on the patient's teeth.

The first tray is preferably made of a clear, thin, flexible material that retains its original shape after placing brackets to the teeth in their ideal position. A second tray is fabricated out of a very rigid, yet thin material and is molded over the first tray during the fabrication process, making the second tray a substantial, supplemental or complimentary duplicate of the first tray.

After the first (flexible) tray has been inserted into the patient's mouth over the teeth, the second (rigid) tray is inserted over the first tray. The second tray stabilizes the first tray and keeps it from moving and holds the brackets, which are temporarily fixed into the first tray, in their ideal position on the teeth until the adhesive bonding material cures and the brackets are secure to the patient's teeth. The second (rigid) tray is then removed. The first tray is then removed by easily peeling the soft flexible material away from the brackets and around the teeth. Since the brackets have been secured to the teeth with adhesive, the brackets will remain on the teeth.

The two tray, indirect bonding system of the present invention thus eliminates drifting of the brackets during insertion of the trays to the mouth and during the curing time required for the adhesive bonding material. Being preferably fabricated of clear materials, the trays allow the clinician a view of the teeth and of vital placement data, such as the clinical midline of the teeth. The trays are low in profile and fabricated out of a thin material, thus being very comfortable to the patient. The bracket-bearing, first tray is flexible enough to be peeled off the patient's teeth. Previous trays had to be cut off in sections, which was a very time-consuming procedure and could aid in pulling off the brackets accidentally. The invention's two tray system can be used to set brackets to the teeth labially or lingually. The trays can also be used as a vehicle for placement of the brackets and auxiliary attachments to all of the teeth from both the labial and lingual sides of the teeth simultaneously.

BRIEF DESCRIPTION OF THE DRAWINGS

For a further understanding of the nature and objects of the present invention, reference should be had to the following detailed description, taken in conjunction with the accompanying drawings in which like parts are given like reference numerals and wherein.

DETAILED DESCRIPTION OF THE PREFERRED EMBODIMENT

Figure 1:
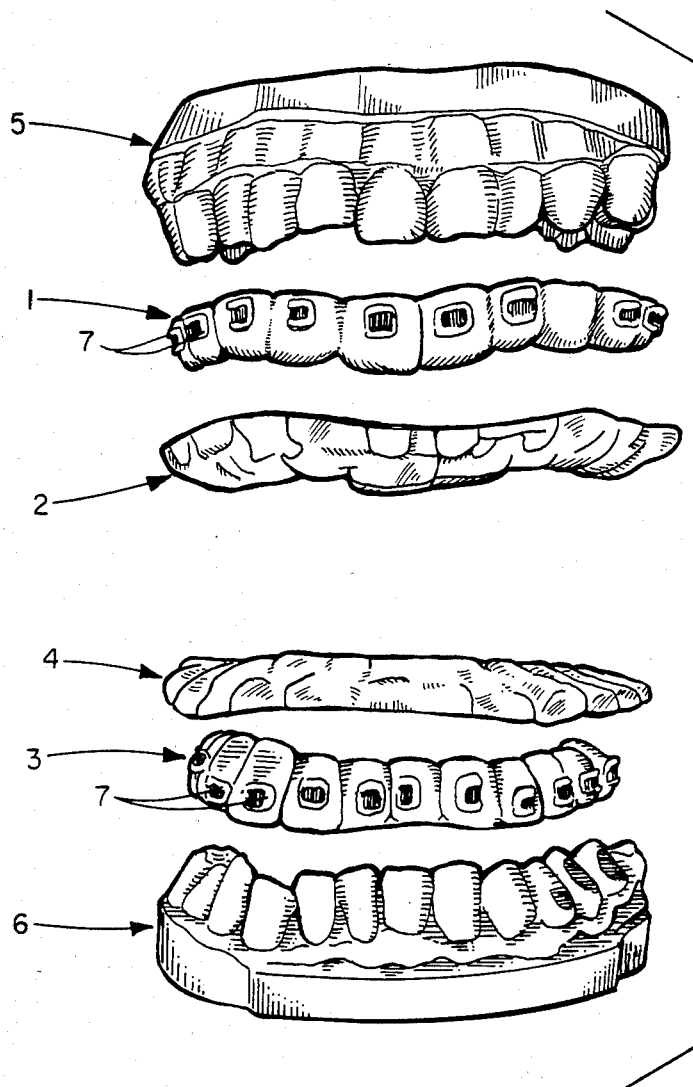
FIG. 1 is an exploded, schematic drawing of the two tray bonding system of the preferred embodiment of the present invention prior to its being attached to the teeth.

Referring to the preferred embodiment of the system of the present invention illustrated in FIG. 1, it can be seen that the molded, upper labial soft tray 1 are only slightly more bulky than the teeth themselves, here represented by dental casts 5 and 6. Similarly, the same may be said of the lower molded lingual tray 3.

Because the soft trays 1, 3 need not be both flexible as well as firm, the range of materials usable is wider, and clear molding materials may be used.

For example, the soft trays 1, 3 may be made of "Bioplast" material available from Great Lakes Orthodontic Products, Inc. of Buffalo, N.Y. (order no. SDB235; square shape, 1.5 mm/125 mm), which has the flexible consistency of rubber and is clear.

The brackets 7 can be seen embedded in the upper soft tray 1 and in the lower soft tray 3 in FIG. 1. Because clear materials may be used, the brackets 7 may be seen during the installation, and the positioning of the brackets 7 on the teeth may be more carefully observed. Additionally, because the material is more flexible, corrections may be made more easily than in the prior art for the minor irregularities of the teeth.

A final but important function attained through the use of the soft trays 1 and 3 is that, during their installation, they may be put on in such a way that the bonding material does not get wiped off. The latter could prevent proper bonding or require extra time and discomfort for the patient, while this material which has set at the time the trays are removed is scrapped or cleaned from the teeth.

The key allowing the flexibility and low profile of the soft tray 1 is the use of a supplemental, molded, relatively hard tray 2, which serves to hold the relatively soft tray 1 in the desired position, after the tray 1 has been fitted over the teeth. Again, hard tray 2 may be very thin, because it may be made of a hard material without worrying about adding the flexibility of the upper soft tray 1. For example, the upper and lower hard trays 2, 4 may be made of "Biocryl 2", also available from Great Lakes Orthodontic Products, Inc. (order no. GL3307; square shape, 2 mm/125 mm), which is clear blue and has the rigidity and appearance of "plex-glass" type material.

The hard trays 2 and 4 are of such design so as to keep the soft trays 1 and 3 in position. Additionally, it is designed so as not to interfere with the position of the tongue. Hence, the patient is left substantially more comfortable during the setting period, both because of the shape and the low profile or lack of bulk in the two tray system of the present invention, even when both sets of trays 1, 2 and 3, 4 are being set at a time. In this way, without undue discomfort of the patient, less professional time is required in the bonding.

When making the molded trays 1–4, the exemplary thermo-plastic materials mentioned, which come in square, flat, sheet form, are placed over the bracketed models and pressume formed to the models, using for example a multi-purpose dental molding machine working on the principle of air pressure. An exemplary machine would be the "Biostart" from Great Lakes (model no. SD062). The soft material under pressure in the machine flows about the brackets 7 and incorporate them into the then molded soft trays 1, 2. The hard trays 2, 4 are then placed in sheet form over the soft molded tray and over the soft trays 1, 3 on the bracketed models.

After the molded materials are cooled, they are trimmed and are ready for use as molded trays. The resulting two tray systems, 1 and 2, and 3 and 4, thus in combination achieve the desired flexibility of the relatively soft material with the incorporated brackets and the desired rigidity of the relatively hard material.

After the two tray systems are molded, they can be used to apply the brackets 7 to the patient's teeth in a fashion analogous to the single tray system of the Cohen et al U.S. Pat. No. 3,738,005 referred to above, the applicable disclosure of which is incorporated herein by reference.

The clinical procedures for indirect bonding in accordance with the preferred embodiment of the present invention are set out below:

A. Case Preparation (1) The patient should have teeth thoroughly cleaned. It is important that the teeth are free of calculus.

(2) No procedure should be initiated that would result in tooth movement between the time of the impressions and seating of the indirect bonding trays. (For example, extraction, separations, etc.)

(3) Alginate impressions should be taken with a rigid, well-fitting impression tray. The impressions should accurately reproduce the plate and all tooth surfaces will clear definition of the gingival crest.

(4) The models 5, 6 should be poured immediately and may be made in yellow stone. Second pour or duplicate models generally are not acceptable. Models should be free of bubbles, chips, voids and trimmed if possible. A flat base is required for accurate measurements.

(5) The brackets 7 are placed according to the manufacturers suggested set up unless otherwise indicated.

B. Seating of Trays (1) The patient is prepared as would be done in the direct bonding method. The teeth are pumiced, dried, etched, dried and sealed.

(2) A composite filling syringe is used to apply bonding material to the bracket bases. A good indirect bonding material should have minimum filler and maximum setting time (e.g. "Auto Tach" bonding material). To increase the setting time, it can be mixed on a cold slab, and, when mixing, a bit more base than catalyst is used.

(3) A small amount of bonding material is then squeezed on to each custom base.

(4) The primary tray 1 (or 3) is then placed in the patient's mouth. The tray is preferably placed buccally first, if labial case, preventing wiping of bonding material from the bases. If case is lingual, the tray is preferably placed lingually first.

(5) The secondary tray 2 (or 4) is immediately placed to insure proper seating of the brackets.

C. Removal of Trays (1) The hard tray 2 (or 4) is removed after proper curing time, and can be easily removed with the fingers.

(2) When removing the soft tray 1 (or 3), an explorer is used to catch the tray gingivally at each bracket, one at a time, and the tray 1 (or 3) is gently peeled away from the brackets.

Of course, the various materials suggested above are merely exemplary and are subject to much variations to achieve the relative softness and flexibility of one tray and the relative hardness and rigidity of the other, supplemental tray. Additionally the material may be molded in other ways, for example by vacuum forming rather than air pressure forming; etc.

Because many varying and different embodiments may be made within the scope of the inventive concept taught herein, and because many modifications may be made in the embodiment(s) herein detailed in accordance with the descriptive requirements of the law, it is to be understood that the details herein are to be interpreted as illustrative and not in a limiting sense.

What is claimed is:

1. An orthodontic method for use in applying brackets to a patient's teeth, comprising the following steps:
    (a) molding a first, relatively soft, flexible tray of the patient's teeth and incorporating into said first tray the brackets properly positioned to be applied to the teeth; and
    (b) molding a second, complementary configured but relatively hard and rigid second tray of the patient's teeth for placement over the exterior of said first tray, providing in supplemental fashion rigidity to the back of said first tray; producing a two tray system which in face-to-face combination has an inner teeth contacting flexibility from said first tray and an outer rigidity from said second tray.

2. The method of claim 1, wherein the method is applied to both the patient's upper and the patient's lower sets of teeth and there is further included the steps of producing a first set of said two tray system for applying a set of brackets on the upper set of teeth and producing a second set of said two tray system for applying a set of brackets on the lower set of teeth thereby producing two sets of said two tray system, one for each bracket set.

3. The method of claim 1, wherein each of said trays includes the step of using a transparent material in molding the trays, producing transparent trays allowing the viewing of the placement of the brackets on the teeth by ther user during the applying of the brackets to the teeth using said two complimentary trays.

4. An orthodontic system for applying brackets to a patient's teeth, comprising:
    (a) a first molded tray molded to the scope of the patient's teeth and incorporating the brackets properly positioned to be applied to the teeth, said first tray being made of relatively soft, flexible material; and
    (b) a second molded tray molded to the back, exterior shape of said first tray, said second tray being made of a relatively hard, rigid material; the two trays in combination with the back, exterior of said first tray in face-to-face engagement with the interior side of said second tray providing a two tray system having an inner, teeth contacting flexibility from said first tray and an outer rigidity from said second tray.

5. The system of claim 4, wherein the materials of both said trays are transparent allowing the user to view the brackets in applying the brackets to the patient's teeth with said two tray system.

* * * * *